US009956071B2

(12) United States Patent
Spenciner et al.

(10) Patent No.: US 9,956,071 B2
(45) Date of Patent: May 1, 2018

(54) ADJUSTABLE LENGTH SURGICAL SCREWS AND INSERTERS FOR ADJUSTABLE LENGTH SURGICAL SCREWS

(71) Applicant: DePuy Mitek, LLC, Raynham, MA (US)

(72) Inventors: David B. Spenciner, North Attleboro, MA (US); Michael S. Varieur, Portsmouth, RI (US)

(73) Assignee: DEPUY MITEK, LLC, Raynham, MA (US)

( * ) Notice: Subject to any disclaimer, the term of this patent is extended or adjusted under 35 U.S.C. 154(b) by 295 days.

(21) Appl. No.: 14/869,058

(22) Filed: Sep. 29, 2015

(65) Prior Publication Data

US 2017/0086966 A1 Mar. 30, 2017

(51) Int. Cl.
*A61F 2/08* (2006.01)
*A61B 17/86* (2006.01)
*A61B 17/00* (2006.01)

(52) U.S. Cl.
CPC .......... *A61F 2/0811* (2013.01); *A61B 17/864* (2013.01); *A61B 17/866* (2013.01); *A61B 17/8645* (2013.01); *A61F 2/0805* (2013.01); *A61B 2017/00473* (2013.01); *A61F 2002/0841* (2013.01)

(58) Field of Classification Search
CPC ............. A61B 17/864; A61B 2090/037; A61F 2/0811; F16B 31/021
See application file for complete search history.

(56) References Cited

U.S. PATENT DOCUMENTS

| 3,675,328 | A | * | 7/1972 | Weissman | A61C 5/35 433/225 |
|---|---|---|---|---|---|
| 6,209,424 | B1 | * | 4/2001 | Croton | F16B 31/021 81/119 |
| 7,604,643 | B2 | | 10/2009 | Ciccone et al. | |
| 7,766,920 | B2 | | 8/2010 | Ciccone et al. | |
| 8,282,651 | B2 | | 10/2012 | Ciccone et al. | |
| 8,523,913 | B2 | | 9/2013 | Jackson | |
| 8,523,914 | B2 | | 9/2013 | Foley et al. | |
| 8,628,537 | B2 | | 1/2014 | Ciccone et al. | |

(Continued)

OTHER PUBLICATIONS

Salhaney, Bob. "Best Methods of Molding Undercuts," Plastics Technology. 1-4 (2012).

(Continued)

*Primary Examiner* — Andrew Yang (57) ABSTRACT

Adjustable length surgical screws and inserters for adjustable length surgical screws and methods of using the screws and inserters are provided. In general, a fixation device such as a surgical screw can be configured to have an adjustable length. The fixation device can have one or more break points along a longitudinal axis thereof. In an exemplary implementation, the fixation device can include a plurality of break points. The plurality of break points can be formed at different predetermined axial positions along the fixation device's longitudinal axis. The fixation device can be configured to break at each of its one or more break points, for example breaking along a plane that is substantially perpendicular to the longitudinal axis of the fixation device.

20 Claims, 5 Drawing Sheets

(56) References Cited

U.S. PATENT DOCUMENTS

| | | |
|---|---|---|
| 8,814,913 B2 | 8/2014 | Jackson |
| 2009/0202387 A1 | 8/2009 | Dlugos, Jr. et al. |
| 2012/0150237 A1 | 6/2012 | Combrowski |

OTHER PUBLICATIONS

"How to Fit Handles," Kitchen Door Workshop Limited. 28-32 (dated no later than Sep. 29, 2015).

"Snap-Off Titanium Screws," Implants International. 1 (2006).

\* cited by examiner

ADJUSTABLE LENGTH SURGICAL SCREWS AND INSERTERS FOR ADJUSTABLE LENGTH SURGICAL SCREWS

FIELD

The present disclosure relates generally to adjustable length surgical screws and inserters for adjustable length surgical screws.

BACKGROUND

The complete or partial detachment of ligaments, tendons, and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities. Surgery may be needed to re-attach the soft tissue to its associated bone or bones.

Some injuries may require surgery to attach two bones and/or bone fragment(s) together, such as in the case of fractured bones.

Numerous devices are currently available to re-attach soft tissue to bone and/or to attach bones or bone fragment(s) together. Examples of such currently available devices include screws, staples, suture anchors, and tacks. For example, in soft tissue re-attachment procedures utilizing screws, the detached soft tissue is typically moved into a tunnel which has been drilled into the bone. Then the screw is passed next to the soft tissue and into the bone, with the compressive forces resulting from inserting the screw holding the soft tissue to the bone.

Depending on the circumstances of the procedure and the variety of physical sizes of patients and locations of repair, a particular screw may be too long or too short for a particular procedure, whether for soft tissue to bone attachment or for bone to bone attachment. Thus, an inventory of screws of varying lengths is typically maintained at hospitals and other surgical facilities. Ensuring that the various lengths are adequately stocked may be time consuming and costly. Additionally, a surgeon typically has to select a length of screw before its implantation, which may complicate the surgical procedure process and/or add to the expense of a surgical procedure.

Accordingly, there remains a need for improved surgical screws and inserters for surgical screws.

SUMMARY

In general, adjustable length surgical screws and inserters for adjustable length surgical screws are provided.

In one aspect, a surgical device is provided that in one implementation includes a fixation device configured to be driven into bone. The fixation device has an exterior surface having a bone-engaging surface feature formed thereon, has a longitudinal axis, and has a plurality of break points at different predetermined axial positions along the longitudinal axis. The fixation device is configured to break at each of the break points such that a proximal portion of the fixation device fully breaks off a distal remainder of the fixation device.

The surgical device can vary in any number of ways. For example, the exterior surface of the fixation device can be uninterrupted by any of the break points.

For another example, at least two of the break points can have a different predetermined break force that, when applied to the fixation device, causes the fixation device to break at the break point. The predetermined break forces can increase from a proximal-most one of the break points to a distal-most one of the break points.

For yet another example, the fixation device can be configured to break at each of the break points along a plane that is substantially perpendicular to the longitudinal axis of the fixation device.

In another example, the fixation device can have an inner cavity formed therein. The inner cavity can be defined by an inner surface of the fixation device. The inner surface can have a plurality of notches formed therein, and each one of the notches can define one of the break points. In another example, the fixation device can have a plurality of weakened regions along the longitudinal axis, and each one of the weakened regions can define one of the break points. In at least some implementations, a sidewall of the fixation device can have a thickness at each of the weakened regions that is less than a thickness of the sidewall at non-weakened regions of the fixation device. In at least some implementations, at least two of the weakened regions can have a different porosity from one another.

In yet another example, the fixation device can have an inner cavity formed therein, and the plurality of break points can include a thread extending longitudinally along a surface defining the inner cavity. At least one of a depth of the thread and a width of the thread can continually decrease in a distal direction.

For another example, the fixation device at each of the break points can be formed from a material different than a material forming a remainder of the fixation device.

As another example, the fixation device can have a plurality of distinct layers stacked along the longitudinal axis. Each of the layers can vary from its one or two adjacent layers in at least one of material and porosity. An interface between each pair of adjacent layers can define one of the break points.

In another aspect, a surgical kit is provided that in one implementation includes the fixation device and an inserter tool configured to drive the fixation device into bone.

The surgical kit can vary in any number of ways. For example, the fixation device can have an inner cavity formed therein, and a distal end of the inserter tool can be configured to be inserted into the inner cavity of the fixation device and rotated to drive the fixation device into bone and cause the fixation device to break at one of the break points. For another example, the inserter tool can be configured to rotate the fixation device to drive the fixation device into bone, the rotation applying a torque to the fixation device and the fixation device being configured to break at each of the break points at a different minimum torque. For yet another example, the fixation device can be configured to be broken at a selected one of the plurality of break points prior to the fixation device being driven into bone by the inserter tool.

In another implementation, a surgical kit is provided that includes a fixation device and an inserter tool. The fixation device has an exterior surface having a bone-engaging surface feature formed thereon, and is configured to break at each of a plurality of different predetermined axial locations therealong. The fixation device breaking at any one of the locations results in a different longitudinal length of the fixation device than the fixation device breaking at any of the other locations. The inserter tool has a distal end configured to be inserted into the fixation device and drive the fixation device into bone by applying a torque force to the fixation device. Each of the plurality of different predetermined axial locations is configured to break at a different torque force applied by the inserter tool to the fixation device.

The surgical kit can vary in any number of ways. For example, the different torque force can increase from a proximal-most one of the locations to a distal-most one of the locations.

In another example, the distal end of the inserter tool can be configured to be inserted into an inner cavity of the fixation device with each of a plurality of different predefined longitudinal lengths therein. In at least some implementations, the inserter tool can include a handle, an elongate shaft extending distally from the handle, and a sheath adjustably disposed on the elongate shaft. A position of the sheath relative to the elongate shaft can define the predefined longitudinal lengths. The sheath can be configured to contact bone and thereby prevent the fixation device from being over-inserted into the bone. In at least some implementations, the inserter tool can include a handle and an elongate shaft extending distally from the handle. The shaft can be movable relative to the handle. A position of the shaft relative to the handle can define the predefined longitudinal lengths.

For another example, the distal end of the inserter tool can be configured to be inserted into an inner cavity of the fixation device. The inserter tool in the inner cavity can be configured to prevent the fixation device from breaking at any of the locations that are proximal to a distal-most end of the inserter tool in the inner cavity.

In another aspect, a surgical method is provided that in one implementation includes manipulating an inserter tool having a distal end positioned within a fixation device so as to apply a force to the fixation device and drive the fixation device into bone. The force applied during the driving of the fixation device into bone causes a proximal portion of the fixation device to break off a remaining distal portion of the fixation device at one of a plurality of predetermined axial locations along the fixation device. The one of the plurality of predetermined axial locations corresponds to an amount of the force. The force includes at least one of a rotational force about a longitudinal axis of the fixation device and a bending force transverse to the longitudinal axis of the fixation device.

The surgical method can vary in any number of ways. For example, the amount of the force that causes the breaking can increase from a proximal-most one of the locations to a distal-most one of the locations. For another example, the fixation device can have a break point formed in an interior surface of the fixation device at each of the plurality of predetermined axial locations. For yet another example, the fixation device can have a plurality of distinct layers stacked along the longitudinal axis, each of the layers can vary from its one or two adjacent layers in at least one of material and porosity, and an interface between each pair of adjacent layers can define the plurality of predetermined axial locations.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various adjustable length surgical screws and inserters for adjustable length surgical screws are provided. In general, a fixation device such as a surgical screw can be configured to have an adjustable length. The fixation device can have one or more break points along a longitudinal axis thereof. In an exemplary implementation, the fixation device can include a plurality of break points. The plurality of break points can be formed at different predetermined axial positions along the fixation device's longitudinal axis. The fixation device can be configured to break at each of its one or more break points, for example breaking along a plane that is substantially perpendicular to the longitudinal axis of the fixation device. The break points can have a variety of configurations, as discussed below, such as notches, undercuts, a thread, a plurality of weakened regions along the longitudinal axis, and/or a plurality of distinct layers stacked along the longitudinal axis. A proximal portion of the fixation device can be configured to fully break off from a distal remainder of the fixation device at each of the fixation device's one or more break points. Each of the fixation device's one or more break points can have a different predetermined break force that, when applied to the fixation device, can be configured to cause the fixation device to break at the break point. The break force can be applied to the fixation device in any of a variety of ways. In at least some implementations, the break force can be in the form of torque caused by rotating the fixation device into bone and/or by shearing force caused by side-to-side bending of the fixation device. The break force for each of a fixation device's plurality of break points can increase from a proximal-most one of the break points to a distal-most one of the break points such that a greater force is required to break the fixation device at a break point positioned farther away from the proximal end of the fixation device than a break point closer to the proximal end of the fixation device. In this way, as greater force is applied to the fixation device, the fixation device can be configured to break first at the proximal-most break point and then at sequentially more distal ones of the break points, thereby allowing the fixation device to have its longitudinal length gradually adjust as force is applied thereto, and/or allowing a distal portion of the fixation device to remain intact for soft tissue fixation while proximal portion(s) of the fixation device break off.

A fixation device having one or more break points along its longitudinal length may allow the fixation device to be used in a surgical procedure without a surgeon or other medical professional having to measure a patient or otherwise predetermine a needed size of fixation device, without a plurality of different sized fixation devices having to be stocked at a hospital or other medical facility, and/or without one of a plurality of differently sized fixation devices being prechosen for implantation. Instead, a single fixation device having an adjustable length can be used, which may save time, save money, and/or allow for greater ease and flexibility in performing a surgical procedure. A fixation device configured to have an adjustable length can have an external surface uninterrupted by its one or more break points, which may allow the fixation device to securely be seated within bone without interference from its break point(s). In other words, the break point(s) may not interfere with one or more bone-engaging features (e.g., threads, ribs, etc.) on the fixation device's external surface, thereby facilitating secure engagement of the bone-engaging feature with bone. A fixation device configured to have proximal portion(s) break off therefrom may allow the device to be implanted before a surgeon or other medical professional has determined the appropriate length of the fixation device, which may save time and/or may help ensure that a fixation device with a wrong length is not used. In contrast, a fixation device having a distal portion that is broken off to change the device's length must be broken before the device is implanted because the distal portion of the fixation device will traditionally be the first portion to be driven into bone.

Figure 1:
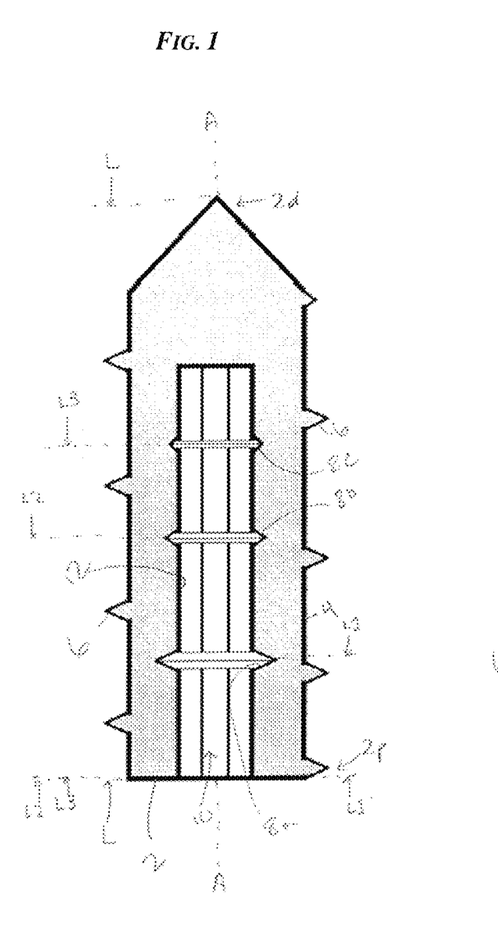
FIG. 1 is a cross-sectional side view of one implementation of a fixation device.
Figure 2:
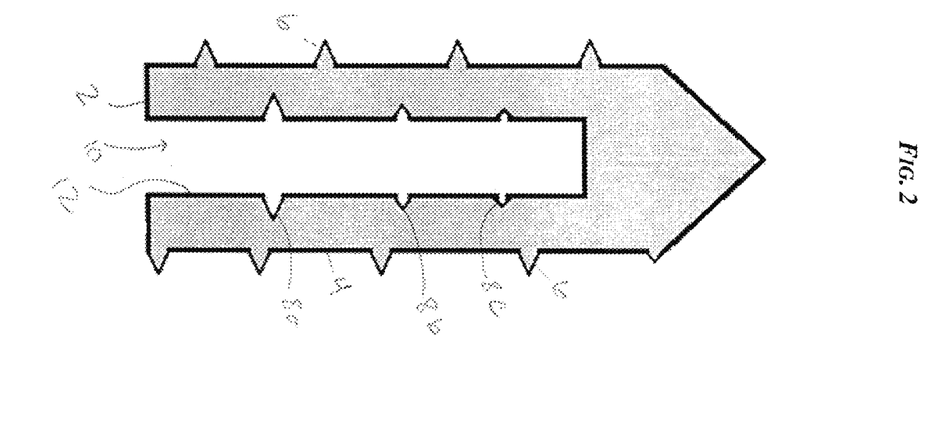
FIG. 2 is another cross-sectional side view of the fixation device of FIG. 1 with a back surface thereof removed for purposes of illustration.

FIGS. 1 and 2 illustrate one implementation of a fixation device 2 configured to have an adjustable length. As shown, the fixation device 2 can have a proximal end 2p and a distal end 2d. The distal end 2d can taper to a point. The fixation device 2 can have an exterior surface 4 with a bone-engaging surface feature 6 thereon. As in this illustrative implementation, the bone-engaging surface feature 6 can include a thread, and the fixation device 2 can include a threaded screw. Other bone-engaging surface features can be used, such as ribs.

The fixation device 2 can include one or more break points 8a, 8b, 8c along a longitudinal length L thereof. The fixation device 2 has three break points 8a, 8b, 8c in this illustrated implementation but can have one, two, four, five, etc. As shown, each break point can be at a different axial position along the longitudinal length L of the fixation device 2. Thus, breakage at different ones of the points 8a, 8b, 8c can result in a fixation device 2 of a different longitudinal length. A first length L1 of the fixation device 2 can be broken off by breaking the fixation device 2 at the first break point 8a, a second length L2 can be broken off by breaking the fixation device 2 at the second break point 8b, and a third length L3 can be broken off by breaking the fixation device 2 at the third break point 8c. The longitudinal lengths L, L1, L2, L3 can have various values. In one implementation, the fixation device's longitudinal length L can be 35 mm, the first length L1 can be 5 mm, the second length L2 can be 8 mm, and the third length L3 can be 12 mm. The fixation device 2 can thus be configured to break into a 30 mm device at the first break point 8a, into a 27 mm device at the second break point 8b, and into a 23 mm device at the third break point 8c. In another implementation, the second length L2 can be 8.5 mm.

Each of the break points 8a, 8b, 8c can be configured to break at a different predetermined break force. The predetermined break force can be lowest for a proximal-most one of the break points 8a and increase for each subsequent break point along the device's longitudinal length L in a distal direction. Thus, the first break point 8a can have the lowest predetermined break force, the second break point 8b can have the next lowest break force, and the third break point 8c can have the highest break force. The fixation device 2 can be configured to break at each of the break points 8a, 8b, 8c by receiving a force as the fixation device 2 is driven into a bone. The proximal-most break point 8a can require less torque force to break compared to the other break points 8b, 8c, with the required torque force increasing to the distal-most break point 8c.

The break points 8a, 8b, 8c can have a variety of configurations. As in this illustrated implementation, each of the break points 8a, 8b, 8c can include a notch in the form of an undercut formed in the fixation device 2. The notches can be positioned along a longitudinal axis A of the fixation device 2 and can be formed in an inner surface 12 of an inner cavity 10 of the fixation device 2. The exterior surface 4 of the fixation device 2 can thus be free of interruption from the break points 8a, 8b, 8c. The inner surface 12 defines the inner cavity 10 within the fixation device 2. Each of the notches can have a different size. The size of each of the notches (e.g., the size of each of the break points 8a, 8b, 8c) can define the predetermined break force for the notch. The notch sizes can vary in depth, in width, or in both depth and width, as in this illustrated implementation. The proximal-most break point 8a has a deepest depth and a largest width, the break point 8b has a shallower depth and a smaller width, and the distal-most break point 8c has the shallowest depth and the smallest width. Accordingly, the deepest depth and the largest width can correspond to the lowest predetermined break force for the fixation device 2, and the shallowest depth and the smallest width can correspond to the highest predetermined break force for the fixation device 2.

The notches can extend circumferentially around the fixation device 2, forming cutout rings in the fixation device 2, as in this illustrative implementation. However, the break points 8a, 8b, 8c can have various other forms. For example the break points 8a, 8b, 8c as notches can be formed by discrete points formed in the inner surface 12 or by partial rings extending around part of the inner surface 12.

The inner cavity 10 in this illustrated implementation has a hexagonal cross-sectional shape. FIG. 1 shows the hexagonal shape of the inner cavity 10, while the hexagonal shape is removed from FIG. 2 for clarity of illustration. The notches at each of the break points 8a, 8b, 8c formed in the inner surface 12 of the fixation device 2 result in weakened regions in the fixation device 2 along the longitudinal length L thereof, with a thickness of the fixation device 2 at each of the weakened regions being less than a thickness of the fixation device 2 at non-weakened regions along the longitudinal length L, e.g., at regions without notches formed therein. The inner cavity 10 can be configured to receive a distal end of an inserter tool therein. Inserter tools (also referred to herein as "inserters") are discussed in more detail below. The inner cavity 10 can have an open proximal end and a closed distal end, as shown in FIGS. 1 and 2, so as to be partially cannulated. However in other implementations, the inner cavity 10 can have open proximal and distal ends such that the fixation device is fully cannulated. The inner cavity 10 has a constant diameter along its longitudinal length in this illustrated implementation but in other implementations can have a varying diameter, e.g., decrease in diameter towards its distal end. Having a varying diameter may facilitate insertion of an inserter tool therein to a correct depth with the inner cavity 10 to facilitate breakage of the fixation device 2 at a selected one of the break points 8a, 8b, 8c, as discussed further below.

A variety of materials can be used to form the fixation device 2, for example one or more of Polyether ether ketone (PEEK), Polylactic acid or polylactide (PLA), BIOCRYL® RAPIDE®, and stainless steel. The fixation device 2 can be formed by a variety of techniques, for example by an injection molding process such as overmolding or by a post-molding process such as post-molding machining.

Figure 3:
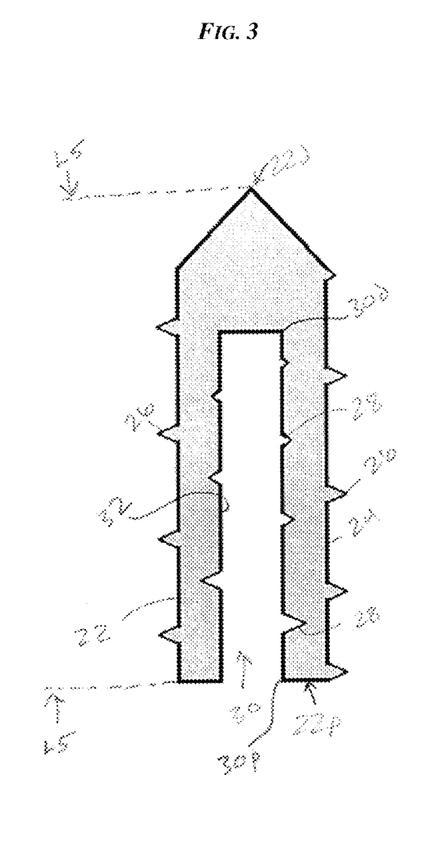
FIG. 3 is a cross-sectional side view of another implementation of a fixation device.

FIG. 3 illustrates another implementation of a fixation device 22 configured to have an adjustable length. The fixation device 22 can generally be configured and used similar to the fixation device 2 of FIGS. 1 and 2, and can have a proximal end 22p and a distal end 22d that can taper to a point, can have an inner cavity 30 defined by an inner surface 32, can have an exterior surface 24 with a bone-engaging surface feature 26 in the form of a thread thereon, and can have one or more break points 28 along a longitudinal length L5 thereof. The one or more break points 28 in this illustrative implementation are in the form of a continuous thread formed longitudinally along the fixation device 22 on the inner surface 32 of the inner cavity 30 of the fixation device 22. As the thread 28 extends from a proximal end 30p of the inner cavity 30 toward a distal end 30d of the inner cavity 30, a size (e.g., depth, width, or depth and width, as in this illustrated implementation) of the thread 28 can decrease so that the thread 28 is largest toward the proximal end 30p and shallowest toward the distal end 30d. The fixation device 22 can be configured to break at the thread 28 similar to that discussed above for the fixation device 2, e.g., by receiving a torque force as the fixation device 22 is driven into a bone. The thread 28 in this illustrated implementation gradually and continuously changes in size along the inner cavity 30. The thread 28 can thus be configured to break at a variety of break forces therealong, with each size corresponding to a different break force. Such a configuration can facilitate use of the fixation device 22 at any of a variety of lengths so as to be accommodating to a large variety of patient anatomies. In another implementation, the thread 28 can have discrete areas of size change therealong. Such a configuration generally corresponds to the implementation of FIGS. 1 and 2 in which notches are formed in the fixation device at discrete points along the device's longitudinal axis A. In other words, each of the discrete areas of the thread 28 can be configured to break at a different predetermined break force, and a proximal discrete area requires less force to break compared to a distal discrete area on the thread of the break points 28.

Figure 4:
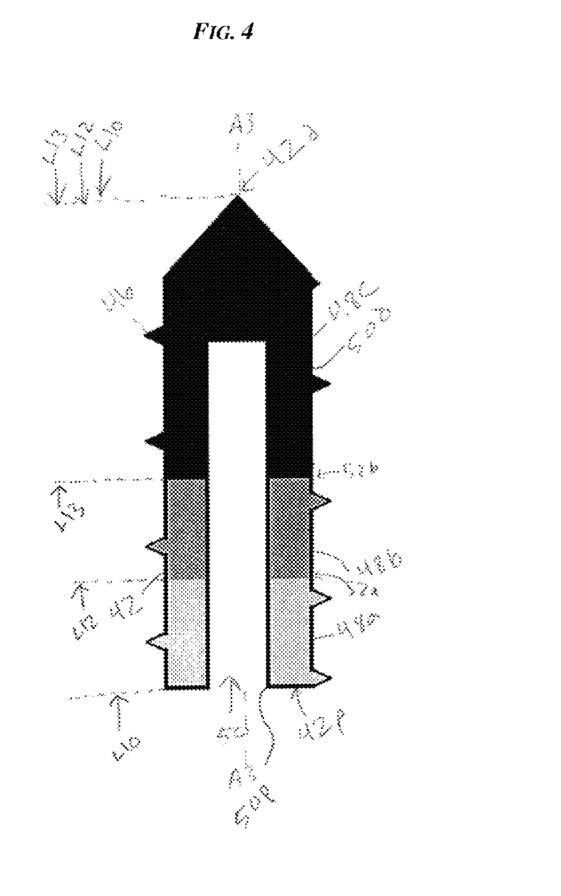
FIG. 4 is a cross-sectional side view of yet another implementation of a fixation device.

FIG. 4 illustrates another implementation of a fixation device 42 configured to have an adjustable length. The fixation device 42 can generally be configured and used similar to the fixation device 2 of FIGS. 1 and 2, but instead of having a break point formed in an inner cavity 50 thereof, the fixation device 42 can be formed from one or more materials that define the fixation device's one or more break points 52a, 52b. The one or more break points 52a, 52b can be defined by the meeting of different materials forming the fixation device 42. The fixation device 42 in this illustrated implementation has three distinct layers 48a, 48b, 48c of material stacked along a longitudinal axis A3 of the fixation device 42 with an interface between each pair of adjacent layers defining the break points 52a, 52b. The fixation device 42 has three layers 48a, 48b, 48c in this illustrative implementation so as to have two break points 52a, 52b, but a fixation device can have another number of layers and a corresponding other number of break points. A material forming each of the layers 48a, 48b, 48c varies from the other layers 48a, 48b, 48c with the proximal-most layer 48a being formed of the weakest material and thereby the easiest to break by applying a force thereto. Materials of the layers 48a, 48b, 48c can get progressively stronger and harder to break with the material of the distal-most layer 48c being the strongest. Thus, each break point 52a, 52b at a different axial position along a longitudinal length L10 of the fixation device 42 can break at a different predetermined force to result in the fixation device 42 having a different longitudinal length. A first length L12 of the fixation device 42 can be created by breaking off the first layer 48a at the first break point 52a. A second length L13 of the fixation device 42 can be created by breaking off the second layer 48b at the second break point 52b. A variety of materials can be used to form the layers 48a, 48b, 48c of the fixation device 42, for example any one or more of PEEK, PLA, BIOCRYL® RAPIDE®, and stainless steel. The fixation device 42 can also be formed by a variety of techniques, for example by an injection molding process such as overmolding.

Layers can be altered in any one or more of a variety of ways to create a variety of different break points. For example, a same material can be used for each layer, but a material property in the material can be varied between neighboring layers, e.g. a density between layers and/or crystallinity. Using density as an example, layers can alternate between being fully dense and having greater porosity, thus decreasing the density in the more porous layers. Break points can thus exist between each layer due to the change in density and each break point can break at a different force depending on the layer's density. For another example, layers can be varied by creating voids in layers and alternating layers with voids and layers without voids, where the break points will occur at the voids. Voids can be hollows created in a molded part. Voids can be caused by material being pulled away from a hot center section towards cold mold walls, leaving a void in the center of the mold. Voids can be created during a molding process through a number of approaches, such as by using smaller gates and/or by chilling an outside of a mold so that any molded material solidifies more quickly at the chilled outer walls. A gate in a molding process can be an opening that allows molten material to be injected into a cavity of a mold. For yet another example, each layer can be molded in a separate step, thereby allowing boundaries to form between each layer where the break points will occur.

In at least some implementations, the interface between each adjacent layer can be weakened in addition to the varying the materials of the layers 48a, 48b, 48c. This weakening (e.g., notches, thinned wall-thickness, etc.) may further encourage breakage of the fixation device 42 at the break points 52a, 52b.

In use, the fixation devices disclosed herein can be used in any number of a variety of surgical procedures and can be driven into a bone in the surgical procedure. For example, the surgical procedure can include a surgical procedure for securing a soft tissue to bone, such as in a rotator cuff repair procedure or an anterior cruciate ligament (ACL) repair procedure.

Figure 5:
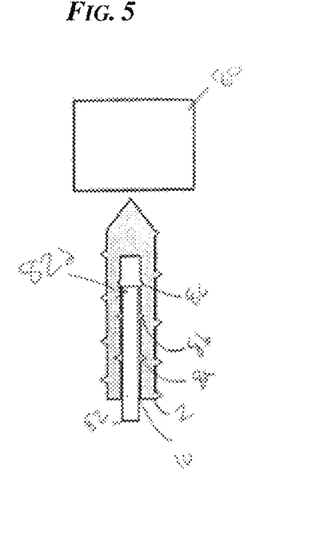
FIG. 5 is a cross-sectional side view of the fixation device of FIG. 1 with an implementation of an inserter advanced to a depth within an inner cavity of the fixation device.
Figures 6, 7:
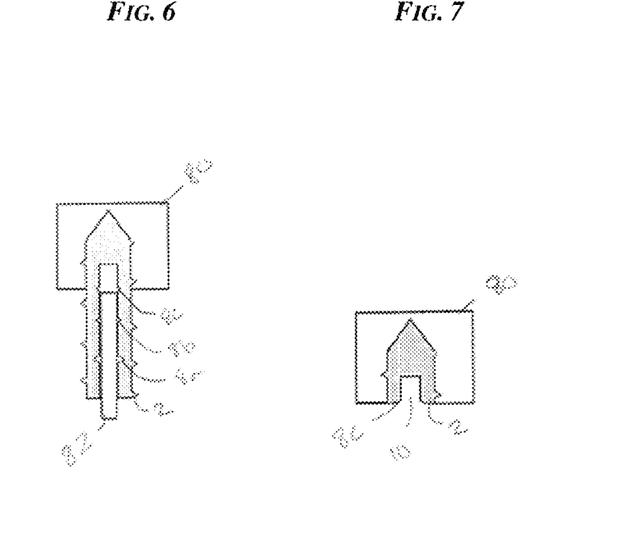
FIG. 6 is a cross-sectional side view of the fixation device of FIG. 5 driven into a schematic representation of bone using the inserter.
FIG. 7 is a cross-sectional side view of the fixation device of FIG. 6 driven into the bone with a proximal portion of the fixation device broken off therefrom.

FIGS. 5-7 illustrate one implementation of using the fixation device 2 of FIG. 1 in a surgical procedure in which the fixation device 2 is advanced into bone 80. Although this implementation is illustrated with respect to the fixation device 2 of FIG. 1, any of the fixation devices disclosed herein can be similarly used. Also, although the fixation device 2 is shown in this implementation being advanced into the bone 80 using one implementation of an inserter 82, any of a variety of inserters can be used to drive the fixation device 2 into the bone 80, such as those discussed further below with respect to FIGS. 11-16.

FIG. 6 shows the inserter 82 inserted into the cavity 10 of the fixation device 2. The inserter 82 can be inserted to a desired depth within the cavity 10, such as to the distal-most break point 8c, as shown in FIG. 5. For another example, the inserter 82 can be inserted to another one of the break points 8a, 8b. A highest torque force applied to a fixation device by an inserter within a cavity of the fixation device is applied at the distal-most end of the inserter. Thus, positioning the inserter's distal-most end adjacent to a one of the break points 8a, 8b, 8c may encourage breakage of the fixation device 2 at that break point. In some implementations, the inserter 82 can be inserted distally past all of the break points 8a, 8b, 8c, e.g., distally past a distal-most one of the break points 8c, to allow a full length of the fixation device 2 to be driven into bone. In other words, the fixation device 2 can be driven into bone using the inserter 82 without the fixation device 2 breaking. In an exemplary implementation, a distal-most end 82d of the inserter 82 within the cavity 10 can be positioned just proximal to one of the break points 8a, 8b, 8c. This positioning may facilitate the breakage of the fixation device 2 at the one of the break points 8a, 8b, 8c (the distal-most break point 8c in the illustrated implementation of FIG. 5) by providing structural integrity to the portion of the fixation device 2 proximal to the one of the break points due to the inserter 82 being within the cavity 10 in that portion of the fixation device 2. In other implementations, the distal-most end 82d of the inserter 82 can be positioned at any position between two adjacent break points. In other implementations, the distal-most end 82d of the inserter 82 can be positioned to be axially aligned with one of the break points 8a, 8b, 8c. This positioning may help encourage breakage of the fixation device 2 at that aligned one of the break points 8a, 8b, 8c by concentrating torque force applied to the fixation device 2 by the inserter 82 at that break point. The one of the break points 8a, 8b, 8c just distal to or axially aligned with the inserter's distal-most end 82d can be pre-selected by a surgeon or other medical practitioner to correspond to a desired broken length of the fixation device 2, e.g., one of the lengths L1, L2, L3 that is less than the fixation device's original length L. The fixation device 2 can thus break to an intended size within a patient.

As shown in FIG. 6, the fixation device 2 having the inserter 82 within the cavity 10 can be driven into the bone 80. The inserter 82 can be rotated about a longitudinal axis thereof, which as shown can be coaxial with the longitudinal axis A of the fixation device 2, to drive the fixation device 2 into the bone 80. As the fixation device 2 is driven into the bone 80, the bone-engaging surface feature 6 can engage the bone 80, e.g., threadably engage the bone 80 in the case of a thread. The fixation device 2 being driven into the bone 80 causes a tunnel to be formed in the bone 80. In other implementations, the tunnel can be pre-formed in the bone 80 using a drill or other tool, as will be appreciated by a person skilled in the art.

The inserter 82 drives the fixation device 2 into the bone 80 with the fixation device 2 at its original length L, as shown in FIG. 6, until a force applied to the fixation device 2 by the inserter 82 reaches a sufficiently high value to cause the fixation device 2 to break at the break point 8c. In other words, the fixation device 2 can remain intact until the predetermined break force associated with the break point 8c is achieved. The inserter 82 being present within the cavity 10 at the axial positions of the break points 8a, 8b having a lower predetermined break force than the break point 8c can prevent the fixation device 2 from breaking at any of the more proximal break points 8a, 8b. The force applied to the fixation device 2 by the inserter 82 can be solely a rotation force as the inserter 82 rotates the fixation device into the bone 2, or the force applied to the fixation device 2 by the inserter 82 can be the rotation force in addition to a shearing force applied to the fixation device 2 by the inserter 82. The shearing force can, as mentioned above, be caused by side-to-side bending of the fixation device 2, such as by moving (e.g., toggling) the inserter 82 side to side. The side to side motion of the inserter 82 can occur, for example, after the fixation device 2 has been rotated a desired depth into the bone 80. In implementations in which an inserter is not rotated to advance a fixation device into a bone, such as when the fixation device does not include a thread but includes another type of bone-engaging feature, such as a plurality of circumferential ribs, the force applied to the fixation device by the inserter to cause breakage of the fixation device can be solely a shearing force.

After the breakage, a distal portion of the fixation device 2 can remain within the bone 80, as shown in FIG. 7. The proximal portion of the fixation device 2, which was proximal to the break point 8*c* and broken off the distal remainder of the fixation device 2 in the bone 80, can be removed from the patient. The fixation device 2 can thus be implanted in the bone 80 with its proximal-most end flush with, sub-flush with, or protruding from a surface of the bone 80, e.g., with a proximal surface of cortical bone that overlays cancellous bone.

Figure 8:
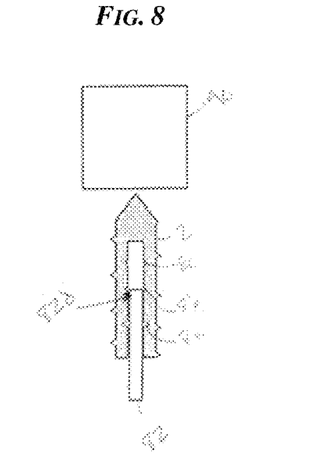
FIG. 8 is a cross-sectional side view of the fixation device of FIG. 1 with the inserter of FIG. 5 advanced to a different depth within the inner cavity of the fixation device.
Figures 9, 10:
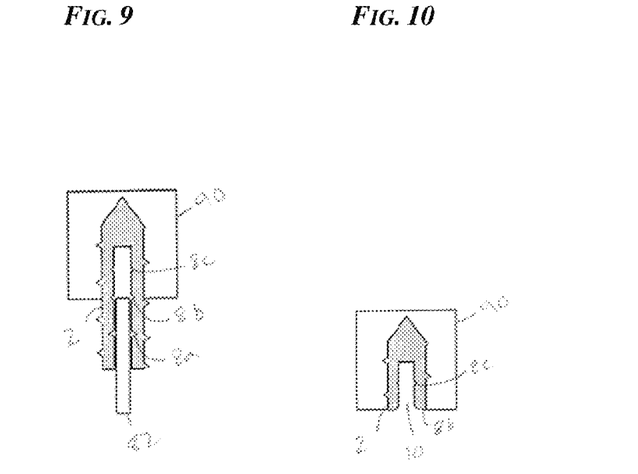
FIG. 9 is a cross-sectional side view of the fixation device of FIG. 8 driven into another schematic representation of bone using the inserter.
FIG. 10 is a cross-sectional side view of the fixation device of FIG. 9 driven into the bone with a proximal portion of the fixation device broken off therefrom.

FIGS. 8-10 illustrate another implementation of using the fixation device 2 and the inserter 82 in a surgical procedure in which the fixation device 2 is advanced into bone 90. FIGS. 8-10 generally correspond to FIGS. 5-7, respectively, except that the distal-most end 82*d* of the inserter 82 is positioned with respect to a different pre-selected one of the break points 8*a*, 8*b*, 8*c*, the middle break point 8*b*. The inserter's distal-most end 82*d* is axially aligned with the selected break point 8*b* in this illustrated implementation such that the fixation device 2 breaks at this break point 8*b*, as shown in FIG. 10.

As mentioned above, any of various inserters can be used to drive a fixation device into bone. An inserter having a distal portion configured to be inserted into a fixation device can allow the fixation device to be driven into a bone and can allow a force (e.g., a rotating force and/or a shearing force) to be applied from the inserter to the fixation device, thereby causing a break in the fixation device at one or more break points along the fixation device's longitudinal length after the inserter has driven the fixation device into the bone. In at least some implementations, the distal portion of the inserter can be inserted into the fixation device's cavity to position by feel the inserter's distal-most end with respect to a pre-selected one of the fixation device's break points. However, this positioning by feel may be challenging for inexperienced users. In at least some implementations, the inserter can have the fixation device pre-loaded on the inserter's distal portion, such as during manufacturing, so as to eliminate the need for a user to load the fixation device onto the inserter by feel. Such pre-loading, however, may increase overall cost because the inserter with pre-loaded fixation device may need to be purchased as a unit for each surgical procedure instead of being purchased individually and/or for re-use. In at least some implementations, the inserter can be configured to have a distal portion that is insertable to a predetermined depth within the fixation device's cavity. The inserter may thus be positioned within the cavity without relying on feel and/or to a constant predetermined depth that accurately positions the inserter's distal-most end with respect to a selected one of the inserter's break points.

In at least some implementations, as mentioned above, an inner cavity of a fixation device can have a distally tapering diameter to facilitate insertion of an inserter tool therein to a correct depth with the inner cavity. The inserter tool can have a modular distal tip in which a plurality of distal tips each having a different diameter are configured to be removably and replaceably attachable to the inserter tool. A one of the distal tips having a diameter corresponding to the diameter of the inner cavity at a desired one of the fixation device's break points can be attached to the inserter tool. The inserter tool's distal end can thus be inserted as far as distally possible within the inner cavity and accordingly be located at the desired one of the break points since the inner cavity's tapering diameter prevents any further distal advancement of the inserter's distal tip. In another implementation, a plurality of inserter tools can be provided, with each of the inserter tools having a distal tip with a different diameter. A one of the inserter tools having a distal tip diameter corresponding to the diameter of the inner cavity at a desired one of the fixation device's break points can be inserted as far as distally possible within the inner cavity and accordingly be located at the desired one of the break points.

Figure 11:
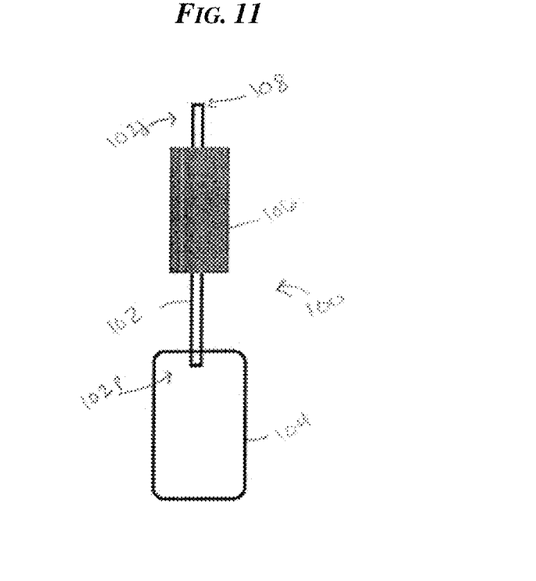
FIG. 11 is a side schematic view of another implementation of an inserter.

FIG. 11 illustrates another implementation of an inserter 100 configured to drive a fixation device into bone. The inserter 100 can generally be configured and used similar to other inserters described herein. As shown, the inserter 100 can have an elongate shaft 102 and can have a handle 104 at a proximal end 102*p* of the shaft 102. The proximal end 102*p* of the shaft 102 can be immovably coupled to the handle 104. The longitudinal shaft 102 can have a distal driving tip 102*d*. The distal driving tip 102*d* can be configured to be inserted into the fixation device, such as by being inserted into an inner cavity of the fixation device. The distal driving tip 102*d* has a hexagonal cross-sectional shape in this illustrated implementation to correspond to a cavity of a fixation device that has a hexagonal cross-sectional shape, but any of a variety of cross-sectional shapes can be used.

The inserter 100 can be configured to be actuated to drive the fixation device into bone in any of a variety of ways. As an example, the inserter 100 can be rotated about a longitudinal axis of the shaft 102 to drive the fixation device coupled to the distal driving tip 102*d*, such as when the fixation device is threaded. For another example, the inserter 100 can be pushed in a distal direction to drive the fixation device coupled to the distal driving tip 102*d* into bone, such as when the fixation device includes ribs. For yet another example, the inserter 100 can be moved side to side to push the fixation device coupled to the distal driving tip 102*d* into bone.

The inserter 100 can be configured to be inserted into a fixation device to a predetermined depth. The inserter 100 can include a sheath 106 configured to be moveable longitudinally along the shaft 102 of the inserter 100 and configured to limit engagement between the inserter 100 and a fixation device. Namely, the sheath 106 can be configured to adjust an amount of the shaft 102 that is insertable into the fixation device by adjusting a length of the distal driving tip 102*d*. The sheath 106 can be configured to be moved to a selected position along the shaft 102 to facilitate insertion of the distal driving tip 102*d* to a particular depth in a fixation device. A distal-most end 108 of the inserter 100 may thus be predictably positioned with respect to break points of the fixation device, e.g., predictably positioned just proximal to or axially aligned with one of the break points. The sheath 106 can be moved longitudinally along the shaft 102 such that a different length of the shaft 102 extends distally from the sheath 106, e.g., such that the distal driving tip 102*d* has a certain length, and has a length equivalent to an amount of the inserter 100 to be inserted into the fixation device to position the inserter's distal-most end 108 therein as desired for fixation device breakage. The distal driving tip 102*d*, having the length, can be inserted into the fixation device until the sheath 106 abuts a proximal end of the fixation device, thereby indicating that the inserter's distal-most end 108 is at the desired location. In other words, the inserter 100 can be known to be at a location to apply force to the fixation device to cause breakage at the desired break point of the fixation device. The sheath 106 can thus be configured as a stop element for the fixation device, with a distal end of the sheath 106 being configured to stop the fixation device when the distal driving tip 102*d* has been inserted into the cavity of the fixation device. The sheath 106 can also be configured as a stop element for the bone in which the fixation device is driven by the inserter 100. As in this illustrated embodiment, the sheath 106 can have a diameter that is greater than a diameter of the shaft 102 and of a fixation device configured to be coupled to the inserter 100, such that the sheath 106 has a larger diameter than a tunnel in the bone having the fixation device therein. The sheath 106 can thus be prevented from entering the tunnel and, consequently, may prevent over-insertion of the fixation device into the bone. The sheath 106 abutting the bone may facilitate breakage of the fixation device due to the interference between the sheath 106 and the bone surface.

The sheath 106 can be configured to be freely slidable along the shaft 102 to any position therealong, which may facilitate use of the inserter 100 with any of a variety of fixation device sizes. The inserter 100 can include a locking mechanism, such as a latch, configured to lock the sheath 106 at a desired position along the shaft 102. Alternatively, the sheath 106 can be configured to move between predetermined points along the shaft's longitudinal axis. For example, the shaft 102 can have a plurality of depressions, notches, and/or other features formed in its surface in which the sheath 106 can be selectively seated, e.g. with a corresponding ball bearing or protrusion of the sheath 106. Each of the features can correspond to a different length of the distal driving tip 102*d*, which in turn can each correspond to a location of the inserter's distal-most end 108 with respect to one of a fixation device's break points. Each of the features can be equidistantly spaced apart from one another, which may allow for predictable motion of the shaft 102 in response to movement of the sheath 106. The seating can be configured to produce a "click" or other noise to indicate proper seating and, hence, proper driving distal tip 102*d* adjustment. For another example, the sheath 106 can be rotatable about the shaft 102, e.g., via threaded connection, to move the sheath 106 longitudinally along the shaft 102. Each 360° rotation of the sheath 106 can correspond to a predetermined length of the driving distal tip 102*d*. The shaft 102 and/or the sheath 106 can include a marking configured to indicate when the sheath 106 has rotated 360°.

Figure 12:
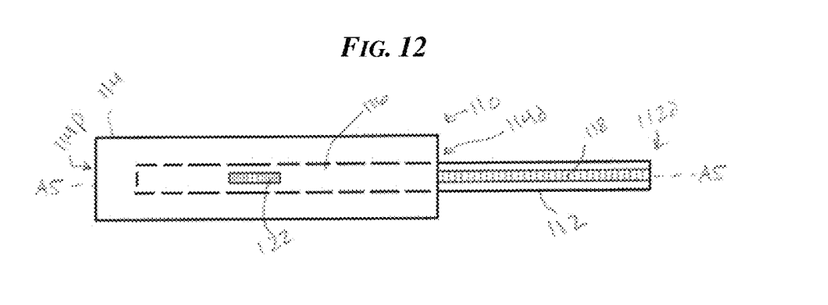
FIG. 12 is a top schematic view of yet another implementation of an inserter.
Figure 13:
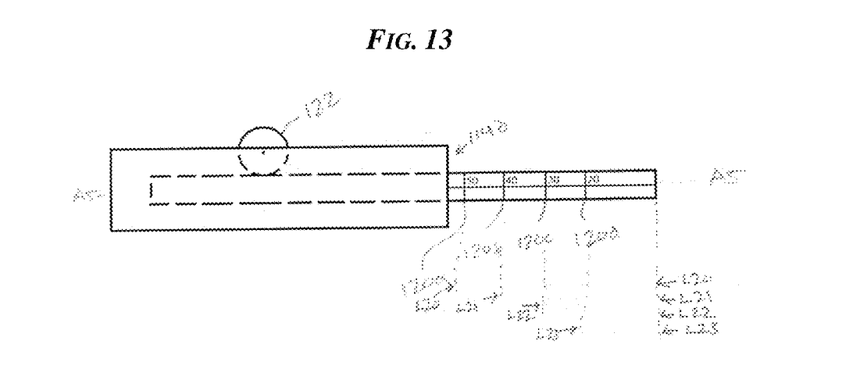
FIG. 13 is a side schematic view of the inserter of FIG. 12.
Figure 14:
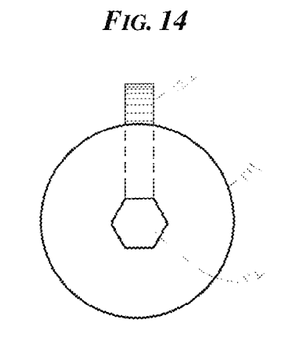
FIG. 14 is a distal end schematic view of the inserter of FIG. 12.

FIGS. 12-14 illustrate another implementation of an inserter 110 configured to drive a fixation device into bone. The inserter 110 can generally be configured and used similar to other inserters described herein and can include an elongate shaft 112 with a distal driving tip 112*d* and a handle 114 at a proximal end of the shaft 112. The handle 114 can have a cavity 116 formed therein extending proximally from the distal end 114*d* of the handle 114 to a position distal of a proximal end 114*p* of the handle 114. In other implementations, the cavity 116 can extend fully through the handle 114 such that the handle 114 is cannulated and able to pass the shaft 112 through both proximal and distal ends 114*p*, 114*d* thereof. A proximal end of the shaft 112 is shown positioned within the cavity 116 in FIGS. 12-14. The shaft 112 can be configured to be moveable (e.g., longitudinally translatable) with respect to the handle 114 so as to adjust a length of the driving distal tip 112*d* extending distally from the handle 114. The shaft 112 can have a plurality of grooves 118 formed therein at a plurality of different axial locations along a longitudinal axis A5 of the shaft 112. The grooves 118 can be configured to individually engage a wheel 122 coupled to the handle 114. The wheel 122 can have a milled edge to facilitate engagement of the wheel 122 with the grooves 118. The wheel 122 can be configured to be manually manipulated and rotated to sequentially engage the grooves 118 and cause the shaft 112 to move proximally and/or distally in and out of the handle 114 along the shaft's longitudinal axis A5. The grooves 118 can be equidistantly spaced apart from one another (e.g., equidistantly spaced ridges and valleys along the shaft 112), which may allow for predictable motion of the shaft 112 in response to movement of the wheel 122. While a wheel and groove mechanism is shown in FIGS. 12-14 to facilitate distal extension of the shaft 112 from the handle 114, any of a variety of mechanisms can be used, such as a rack and pinion mechanism or a friction fit between a wheel and a shaft.

The shaft 112 can have a plurality of measurement marks 120*a*, 120*b*, 120*c*, 120*d* thereon that indicate a fixation device size (e.g., length) aligned with the distal end 114*d* of the handle 114. For example, the wheel 122 can be rotated to move the shaft 112 to align the "50" measurement mark 120*a* with the distal end 114*d* of the handle 114 to indicate that the shaft 112 at that position corresponds to a broken fixation device length of 50 mm. Once the alignment occurs, a length L20 of the shaft 112 extends distally beyond the handle 114. The distal driving tip 112*d* can be inserted into a fixation device and force can be applied at a depth in the fixation device of L20. The measurement marks 120*a*, 120*b*, 120*c*, 120*d* can allow lengths L20, L21, L22, L23 of the shaft 112 to extend distally beyond the handle 114. The measurement marks 120*a*, 120*b*, 120*c*, 120*d* can be made to correspond with break points in a fixation device so that the shaft 112 can be moved to a desired length to ensure force will be applied at a desired break point within the fixation device. The measurement marks 120*a*, 120*b*, 120*c*, 120*d* can correspond to various lengths to correspond to various possible lengths of fixation devices that may be used with the inserter 110. For example, the measurement marks 120*a*, 120*b*, 120*c*, 120*d* in this illustrated implementation, as shown in FIG. 13, correspond to lengths of 20 mm, 30 mm, 40 mm, and 50 mm. As shown in FIG. 14, the shaft 112 has a hexagonal cross-sectional shape, but other cross-sectional shapes can be used.

Figure 15:
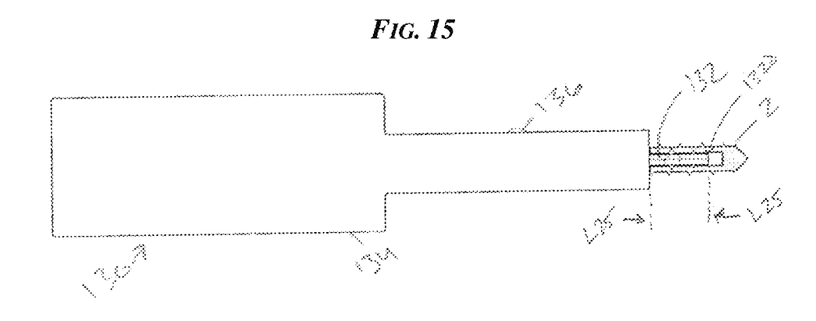
FIG. 15 is a partial cross-sectional, side schematic view of another implementation of an inserter having the fixation device of FIG. 1 coupled to a distal end thereof.

FIG. 15 illustrates another implementation of an inserter 130 configured to drive a fixation device into bone. The inserter 130 can generally be configured and used similar to other inserters described herein and can have an elongate shaft 132 with a distal driving tip 132*d* having grooves and measuring marks, can have a handle 134, and can have a wheel 136 configured to rotate to longitudinally move the shaft 132 proximally and/or distally in and out of the handle 134. The handle 134 can have a tapered distal portion including the wheel 136 and a proximal portion configured to be handheld by a user with a thumb of the hand manipulating the wheel 136 (e.g., rolling the wheel clockwise and counterclockwise to move the shaft 132 proximally and distally relative to the handle 134. A length L25 of the shaft 132, e.g., the distal driving tip 132*d*, extends distally beyond the handle 134, and the distal driving tip 132*d* with the length L25 can be inserted into a fixation device with the length L25 corresponding to place the distal driving tip 132*d* at a break point of a fixation device, for example the break point 8*c* in the fixation device 2 as shown in FIG. 15.

Figure 16:
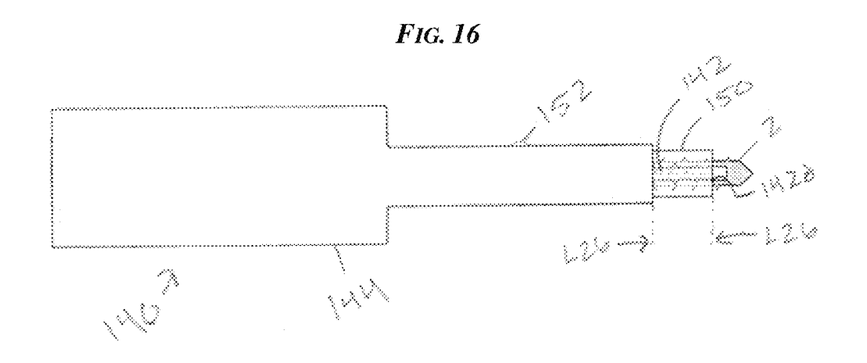
FIG. 16 is a partial cross-sectional, side schematic view of another implementation of an inserter having the fixation device of FIG. 1 coupled to a distal end thereof.

FIG. 16 illustrates still another implementation of an inserter 140 configured to drive a fixation device into bone. The inserter 140 can generally be configured and used similar to other inserters described herein. The inserter 140 can have an elongate shaft 142 with a distal driving tip 142*d* having grooves and measuring marks, can have a handle 144, and can have a wheel 152 configured to rotate to longitudinally move the shaft 142 proximally and/or distally in and out of the handle 144. A length L26 of the shaft 142, e.g., the distal driving tip 142*d*, extends distally beyond the handle 144, and the distal driving tip 142*d* can be inserted into a fixation device, such as the fixation device 2 of FIG.

1 as illustrated in FIG. 16, with the length L25 corresponding to a desired break point of the fixation device 2, for example the break point 8c in the fixation device 2 as shown.

As shown, the inserter 140 can include a sheath 150 extending distally from the handle 144 and positioned around the shaft 142 outside the handle 144, e.g., around a proximal portion of the distal driving tip 142d extending distally from the handle 144. The sheath 150 can thus be configured to be positioned around a proximal portion of the fixation device 2 coupled to the inserter 140. The sheath 140 can be configured to help initially align the inserter 140 and the fixation device 2 by preventing the fixation device 2 from being over-inserted onto the inserter 140, similar to the sheath 106 discussed above with respect to FIG. 11. The sheath 150 can be configured to hold therein a proximal portion of the fixation device 2 that breaks off the fixation device 2 after the inserter 140 has driven the fixation device 2 into bone. The broken-off proximal portion of the fixation device 2 may thus be easier to remove from the patient's body and/or be less likely to cut or otherwise interfere with any tissue and/or other surgical tools adjacent thereto after breakage.

The sheath 150 can be configured to move with the shaft 142 in response to manipulation of the wheel 152 such that a same amount of the shaft 142 is disposed within the sheath 150 regardless of the length L26 of the shaft 142 that extends distally from the handle 144. The sheath 150 may thus be more able to capture the broken proximal portion of the fixation device 2 therein since the proximal portion can be disposed therein regardless of the size of the fixation device 2. Alternatively, the sheath 150 can be fixedly mounted to the handle 144 such that manipulation of the wheel 152 moves the shaft 142 relative to the handle 144 and to the sheath 142.

As shown, the sheath 150 can terminate at a location that is proximal to a distal-most end of the shaft 142. The fixation device 2 may thus be more easily broken since the distal end of the shaft 142 can be located at or adjacent to the desired break point distal to the sheath 150. Alternatively, the sheath 150 can have approximately the same length L26 as the shaft 142 protruding from the handle 144 such that only a distal tip of the fixation device 2 coupled to the inserter 140 extends distally from the sheath 150.

In at least some implementations, an inserter tool can be used to insert a fixation device into bone first for measurement purposes and then be removed from the fixation device before being inserted into the fixation device again for fixation device breakage and implantation purposes. In other words, the inserter can fully insert the fixation device into an intended depth in the bone, then the inserter can be removed from the fixation device and the fixation device size and/or the bone tunnel depth can be measured, then the inserter can be re-inserted into the fixation device to break the fixation device. The inserter may thus be accurately positioned relative to the most appropriate one of the break points prior to breakage of the fixation device, e.g., by side-to-side motion of the inserter. In order to help prevent unintentional breakage of the fixation device during insertion of the fixation device into bone for measurement purposes, the tunnel can be pre-formed, the inserter can be used to push the fixation device into the bone without rotation or toggling of the inserter, and/or the inserter cannot be moved side to side to apply a shearing force to the fixation device until breakage of the fixation device is intended.

In at least some implementations, an inserter can be configured to form a continuous thread in a fixation device, e.g., in an inner cavity thereof. The inserter can thus be configured to at least partially form one or more break points in the fixation device. The fixation device may thus be easier to manufacture than a fixation device that has its one or more break points fully pre-formed therein, such as the fixation devices 10, 22 of FIGS. 1 and 3. The inserter being configured to at least partially form the one or more break points the form of a continuous thread in the fixation device may allow the fixation device's broken length to be selected as any length by a user, which may facilitate use of the fixation device in any of a variety of situations with any of a variety of different types and sizes of patient anatomies.

The inserter can be configured to at least partially form a continuous thread in a fixation device in a variety of ways. For example, the inserter can have an outward facing tooth at a distal end thereof configured to cut a continuous thread in an inner cavity of a fixation device when inserted into the inner cavity and rotated therein. The fixation device can have a start of the continuous thread pre-formed therein to act as an initial guide for the tooth before the tooth begins cutting the thread in the fixation device, e.g., before the tooth continues the thread distally within the inner cavity. Alternatively, the fixation device can be fully free of any pre-formed thread therein such that the tooth fully forms the continuous thread.

Instead of the inserter being configured to at least partially form the continuous thread in the fixation device, another tool such as an elongate shaft having an outward-facing tooth at a distal end thereof can be used to form the continuous thread in the fixation device similar to that discussed above. The shaft can then be removed from the fixation device and the inserter inserted in the fixation device for driving the fixation device into bone.

In at least some implementations, a fixation device can be broken prior to the fixation device being driven into a patient's bone with an inserter tool. The fixation device can be securely held by a clamp, by hand, and/or other holding mechanism outside of the patient and have force applied thereto to break the fixation device at one of its break points. For example, the fixation device can be manually snapped at a selected one of the fixation device's break points. After the fixation device has had a proximal portion thereof broken off, the fixation device can be coupled to an inserter tool and driven into bone. A proper size of inserter may thus be selected for the specific size of the fixation device, already at its implanted size before being implanted in the patient.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a fixation device configured to be driven into bone, the fixation device having an exterior surface having a bone-engaging surface feature formed thereon, the fixation device having a longitudinal axis, the fixation device having a plurality of break points at different predetermined axial positions along the longitudinal axis, and the fixation device being configured to break at each of the break points such that a proximal portion of the fixation device fully breaks off a distal remainder of the fixation device,
wherein the fixation device has an inner cavity formed therein, the inner cavity being defined by an inner surface of the fixation device, the inner surface having a plurality of notches formed therein, each one of the notches defining one of the break points.

2. The device of claim 1, wherein the exterior surface of the fixation device is uninterrupted by any of the break points.

3. The device of claim 1, wherein at least two of the break points have a different predetermined break force that, when applied to the fixation device, causes the fixation device to break at the break point.

4. The device of claim 3, wherein the predetermined break forces increase from a proximal-most one of the break points to a distal-most one of the break points.

5. The device of claim 1, wherein the fixation device is configured to break at each of the break points along a plane that is substantially perpendicular to the longitudinal axis of the fixation device.

6. The device of claim 1, wherein the fixation device has a plurality of weakened regions along the longitudinal axis, each one of the weakened regions defining one of the break points.

7. A surgical kit, comprising:
the fixation device of claim 1; and
an inserter tool configured to drive the fixation device into bone.

8. The kit of claim 7, wherein a distal end of the inserter tool is configured to be inserted into the inner cavity of the fixation device and rotated to drive the fixation device into bone and cause the fixation device to break at one of the break points.

9. A surgical device, comprising:
a fixation device configured to be driven into bone, the fixation device having an exterior surface having a bone-engaging surface feature formed thereon, the fixation device having a longitudinal axis, the fixation device having a plurality of break points at different predetermined axial positions alone the longitudinal axis, and the fixation device being configured to break at each of the break points such that a proximal portion of the fixation device fully breaks off a distal remainder of the fixation device,
wherein the fixation device has an inner cavity formed therein, and the plurality of break points includes a thread extending longitudinally along a surface defining the inner cavity, at least one of a depth of the thread and a width of the thread continually decreasing in a distal direction.

10. The device of claim 9, wherein at least two of the break points have a different predetermined break force that, when applied to the fixation device, causes the fixation device to break at the break point.

11. The device of claim 10, wherein the predetermined break forces increase from a proximal-most one of the break points to a distal-most one of the break points.

12. The device of claim 9, wherein the fixation device is configured to break at each of the break points along a plane that is substantially perpendicular to the longitudinal axis of the fixation device.

13. A surgical device, comprising:
a fixation device configured to be driven into bone, the fixation device having an exterior surface having a bone-engaging surface feature formed thereon, the fixation device having a longitudinal axis, the fixation device having a plurality of break points at different predetermined axial positions along the longitudinal axis, and the fixation device being configured to break at each of the break points such that a proximal portion of the fixation device fully breaks off a distal remainder of the fixation device,
wherein the fixation device at each of the break points is formed from a material different than a material forming a remainder of the fixation device.

14. The device of claim 13, wherein the exterior surface of the fixation device is uninterrupted by any of the break points.

15. The device of claim 13, wherein at least two of the break points have a different predetermined break force that, when applied to the fixation device, causes the fixation device to break at the break point.

16. The device of claim 15, wherein the predetermined break forces increase from a proximal-most one of the break points to a distal-most one of the break points.

17. A surgical kit, comprising:
the fixation device of claim 13; and
an inserter tool configured to drive the fixation device into bone.

18. A surgical device, comprising:
a fixation device configured to be driven into bone, the fixation device having an exterior surface having a bone-engaging surface feature formed thereon, the fixation device having a longitudinal axis, the fixation device having a plurality of break points at different predetermined axial positions along the longitudinal axis, and the fixation device being configured to break at each of the break points such that a proximal portion of the fixation device fully breaks off a distal remainder of the fixation device, wherein the fixation device has a plurality of distinct layers stacked along the longitudinal axis, each of the layers varying from its one or two adjacent layers in at least one of material and porosity, and an interface between each pair of adjacent layers defining one of the break points.

19. The device of claim 18, wherein at least two of the break points have a different predetermined break force that, when applied to the fixation device, causes the fixation device to break at the break point.

20. The device of claim 18, wherein the fixation device has a plurality of weakened regions along the longitudinal axis, each one of the weakened regions defining one of the break points.

* * * * *